US010175140B1

United States Patent
Ho et al.

(10) Patent No.: US 10,175,140 B1
(45) Date of Patent: Jan. 8, 2019

(54) PORTABLE LUMINESCENCE DETECTOR COMBINED WITH A MOBILE DEVICE

(71) Applicant: Soochow University, Taipei (TW)

(72) Inventors: Mei-Lin Ho, Taipei (TW); Chun-Yen Lin, New Taipei (TW); Wei-Ren Lin, Taipei (TW); Ying-Chu Wang, Changhua County (TW); Kuen-Yuh Chung, New Taipei (TW)

(73) Assignee: SOOCHOW UNIVERSITY, Taipei (TW)

( * ) Notice: Subject to any disclaimer, the term of this patent is extended or adjusted under 35 U.S.C. 154(b) by 0 days.

(21) Appl. No.: 15/800,067

(22) Filed: Nov. 1, 2017

(30) Foreign Application Priority Data

Sep. 4, 2017 (TW) .............................. 106130102 A (51) Int. Cl.
| | |
|---|---|
| *G01N 21/25* | (2006.01) |
| *G01M 11/02* | (2006.01) |
| *H04N 5/225* | (2006.01) |
| *G01J 3/02* | (2006.01) |
| *G03B 17/56* | (2006.01) |
| *G01J 3/50* | (2006.01) |
| *G01N 21/64* | (2006.01) |
| *G01J 1/42* | (2006.01) |
| *G01J 3/12* | (2006.01) |

(52) U.S. Cl.
CPC .......... *G01M 11/0207* (2013.01); *G01J 3/02* (2013.01); *G01J 3/505* (2013.01); *G01N 21/6428* (2013.01); *G03B 17/565* (2013.01); *H04N 5/2254* (2013.01); *G01J 2001/4233* (2013.01); *G01J 2003/1239* (2013.01)

(58) Field of Classification Search
CPC ......... G01J 3/02; G01J 3/505; G01M 11/0207
USPC ......................................................... 356/417
See application file for complete search history.

(56) References Cited

U.S. PATENT DOCUMENTS

| | | | |
|---|---|---|---|
| 2013/0130369 A1* | 5/2013 | Wilson ................ | B01L 3/50825 435/289.1 |
| 2015/0241353 A1* | 8/2015 | Oki .................... | B01L 3/502715 436/501 |
| 2016/0011114 A1* | 1/2016 | Oki ........................ | G01N 21/03 435/7.21 |

* cited by examiner

*Primary Examiner* — Sunghee Y Gray
(74) *Attorney, Agent, or Firm* — Chun-Ming Shih (57) ABSTRACT

The present invention provides a portable luminescence detector combined with a mobile device, which mainly comprises a body, a focusing lens module, a light source module, a sample tray, and an image capturing module, wherein the image capturing module can be a lens of the mobile device, the body can be disassembled into multiple parts to act as holders for the portable luminescence detector. When the portable luminescence detector of the present invention is used in conjunction with the mobile device, the sample tray is placed at a position corresponding to that of the focusing lens module, and the light source module is used for providing a light source band, then the image capturing module works with the focus lens module to capture an image of the sample under the light source band and to provide the image for RGB spectral analysis or real-time image RGB spectral analysis.

9 Claims, 7 Drawing Sheets

PORTABLE LUMINESCENCE DETECTOR COMBINED WITH A MOBILE DEVICE

BACKGROUND OF THE INVENTION

This application claims priority benefit of TW Patent Application Ser. No. 106130102 filed 2017 Sep. 4 which is hereby incorporated herein by reference in its entirety.

1. Field of the Invention

The present invention relates to a luminescence detector, and more particularly, to a portable luminescence detector which can be combined with a mobile device and use the mobile device as an image capturing module.

2. Description of the Prior Art

In order to achieve real-time monitoring and to keep track of physical conditions of people in high-risk groups for diseases or patients, recently fluorescence detectors are commonly used in clinical practices as medical detection equipment. However, regarding to home care, outdoor environment or portable applications, existing fluorescent detectors are not applicable because they tend to be bulky and occupy a lot of space, and they can only be operated by technical staff; therefore, it has become an object to find a fluorescence or luminescence detector which is small and easy to carry, and can also provide fast and accurate measurement results.

SUMMARY OF THE INVENTION

In order to solve the problems encountered in the prior art and to achieve the above object, the present invention provides a portable luminescence detector which can be combined with a mobile device. The portable luminescence detector is small and easy to carry, and can also provide fast and accurate measurement results.

The present invention provides a portable luminescencee detector combined with a mobile device, the portable luminescence detector comprises a body comprising a first main body, a second main body, a focusing lens module, a sample tray slideway, a sample tray, a light source module, and a first accommodating space. The first main body is disposed with a through hole which penetrates from a first side of the first main body to a second side of the first main body; the focusing lens module is disposed in the through hole; the first accommodating space and the sample tray slideway are disposed at the second side of the first main body, wherein the first accommodating space is disposed between the second side of the first main body and the sample tray slideway, and the light source module is disposed in the first accommodating space. The sample tray passes through the sample tray slideway opening from an edge of the first main body to be disposed in the first accommodating space and located between the through hole and the sample tray slideway.

The present invention further comprises an image capturing module which is disposed at a camera of a mobile device, a digital camera, or a microscope, wherein the image capturing module is disposed at the first side of the first main body, and the image capturing module works with the focusing lens module to capture an image of the sample tray on the second side of the first main body through the through hole. Furthermore, a lens of the image capturing module forms a tilted angle with the light source module.

In the present invention, the first side of the second main body is a plane, and a second side of second main body comprises a second accommodating space. The second side of the first main body is connected with the second side of the second main body through a plurality of combining portions, wherein the plurality of combining portions can be magnets or buckles. When the first main body and the second main body are combined into a cube, the sample tray can be accommodated in the second accommodating space.

The second main body further comprises a first supporting block and a second supporting block, wherein the first supporting block is connected with the second supporting block through a plurality of support joints, and the plurality of support joints can be magnets or buckles. When performing a luminescence detection, the first support block and the second supporting block can be placed anywhere on the camera of the mobile device, digital camera or microscope to support and to keep the image capturing module in balance.

The light source module is powered by a battery disposed therein, and the light source module can be a light emitting diode (LED) that can switch between different light emitting wavelengths according to different samples.

BRIEF DESCRIPTION OF THE DRAWINGS

For a better understanding of the aforementioned embodiments of the invention as well as additional embodiments thereof, reference should be made to the Description of Embodiments below, in conjunction with the following drawings in which like reference numerals refer to corresponding parts throughout the figures.

DETAILED DESCRIPTION OF THE PREFERRED EMBODIMENT

The following description is about embodiments of the present invention; however it is not intended to limit the scope of the present invention.

Figure 1:
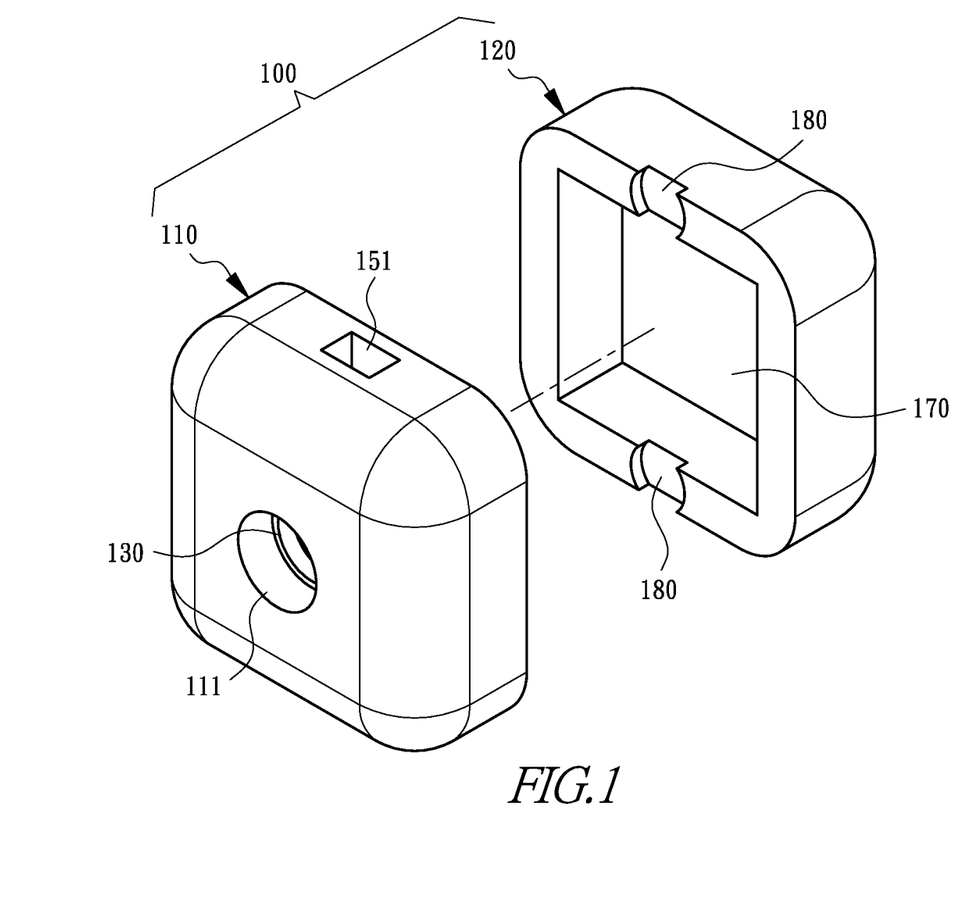
FIG. 1 illustrates a view of a portable luminescence detector combined with a mobile device disclosed in the present invention.
Figure 2:
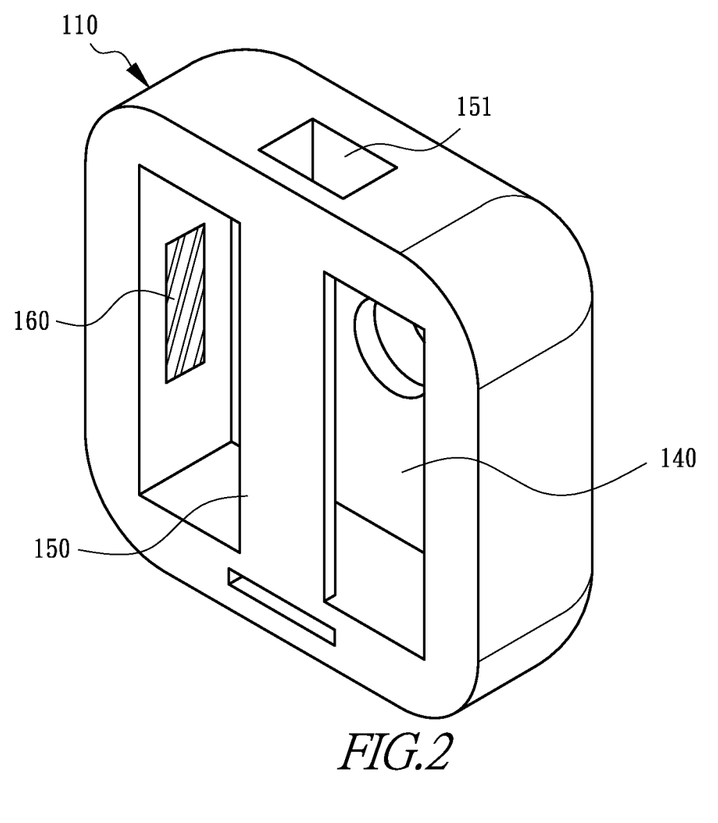
FIG. 2 illustrates a view of a first main body of the portable luminescence detector combined with the mobile device disclosed in the present invention.
Figure 3:
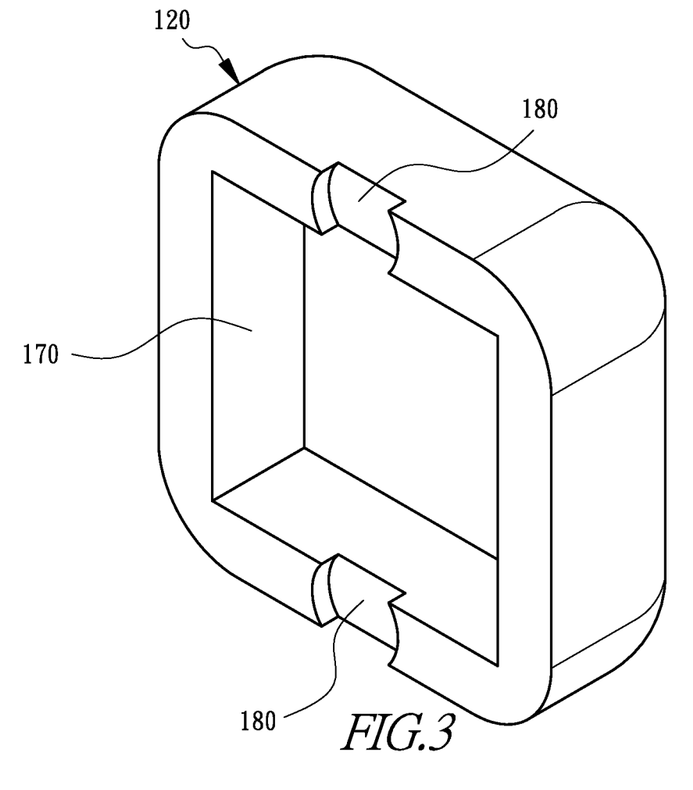
FIG. 3 illustrates a view of a second main body of the portable luminescence detector combined with the mobile device disclosed in the present invention.

Please refer to FIG. 1 to FIG. 3 for views of a portable luminescence detector which can be combined with a mobile device. In the figures, a body 100 comprises a first main body 110, a second main body 120, a focusing lens module 130, a first accommodating space 140, a sample tray slideway 150, a light source module 160, a second accommodating space 170, and a combining portion 180. The first main body 110 is disposed with a through hole 111 penetrating from a first side of the first main body 110 to a second side, and the focusing lens module 130 is disposed in the through hole 111. As shown in FIG. 2, a first accommodating space 140 and a sample tray slideway 150 are disposed at the second side of the first main body 110, wherein the first accommodating space 140 is disposed at the second side of the first main body 110 and the sample tray slideway 150, and a sample tray slideway opening 151 is disposed at an edge of the first main body 110 and corresponds to the sample tray slideway 150. The light source module 160 is disposed in the first accommodating space 140, wherein the light source module 160 is powered by a battery disposed therein, and the light source module 160 can be a light emitting diode (LED) that can switch between different light emitting wavelengths according to different samples. As shown in FIG. 3, the first side of the second main body 120 is a plane, and a second side of second main body 120 comprises a second accommodating space 170. The first main body 110 is connected with the second main body 120 through a plurality of combining portions 180, wherein the plurality of combining portions 180 can be magnets or buckles.

Figure 4:
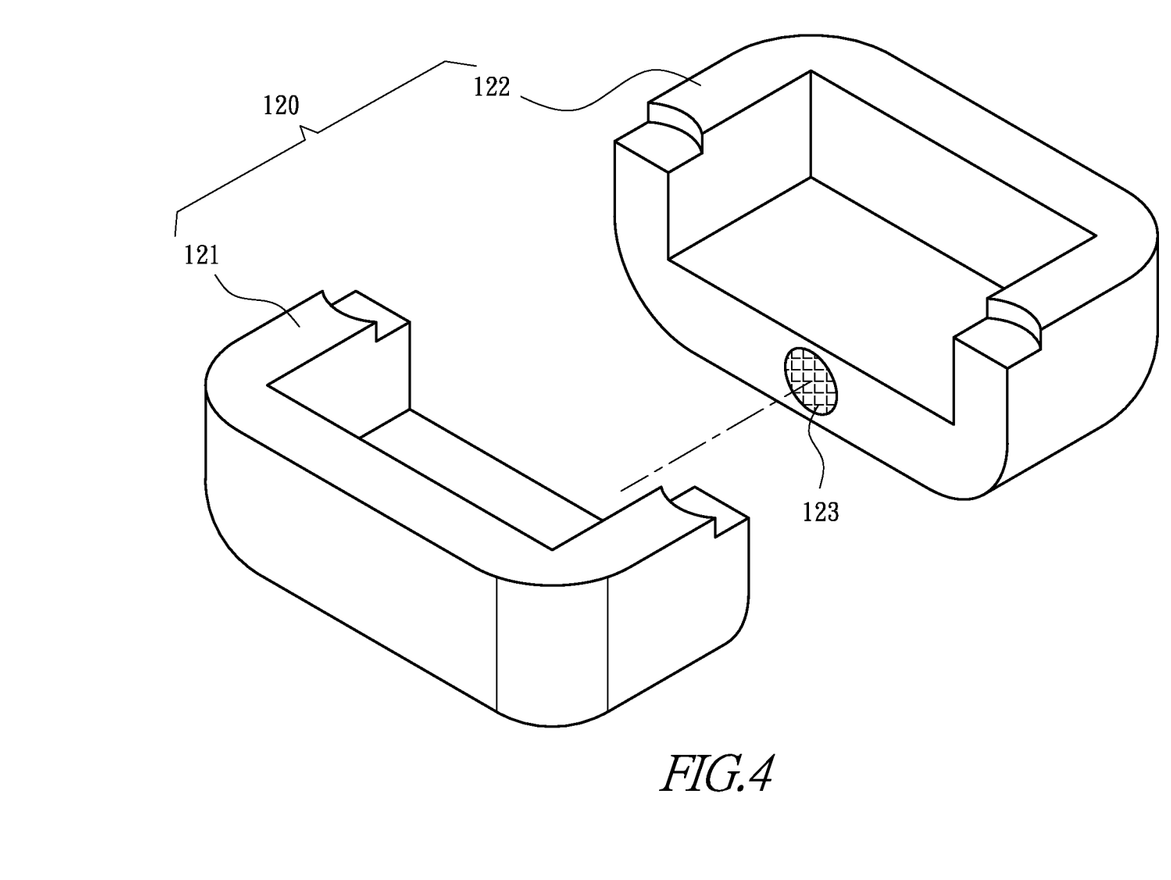
FIG. 4 illustrates a view of supporting blocks of the portable luminescence detector combined with the mobile device disclosed in the present invention.

As shown in FIG. 4, the second main body 120 can be dissembled into a first supporting block 121 and a second supporting block 122, wherein the first supporting block 121 is connected with the second supporting block 122 through a plurality of support joints 123, and the plurality of support joints 123 can be magnets or buckles. When performing a luminescence detection, the first support block 121 and the second supporting block 122 can be placed anywhere on the camera of the mobile device, digital camera or microscope to support and to keep the image capturing module in balance.

Figure 5:
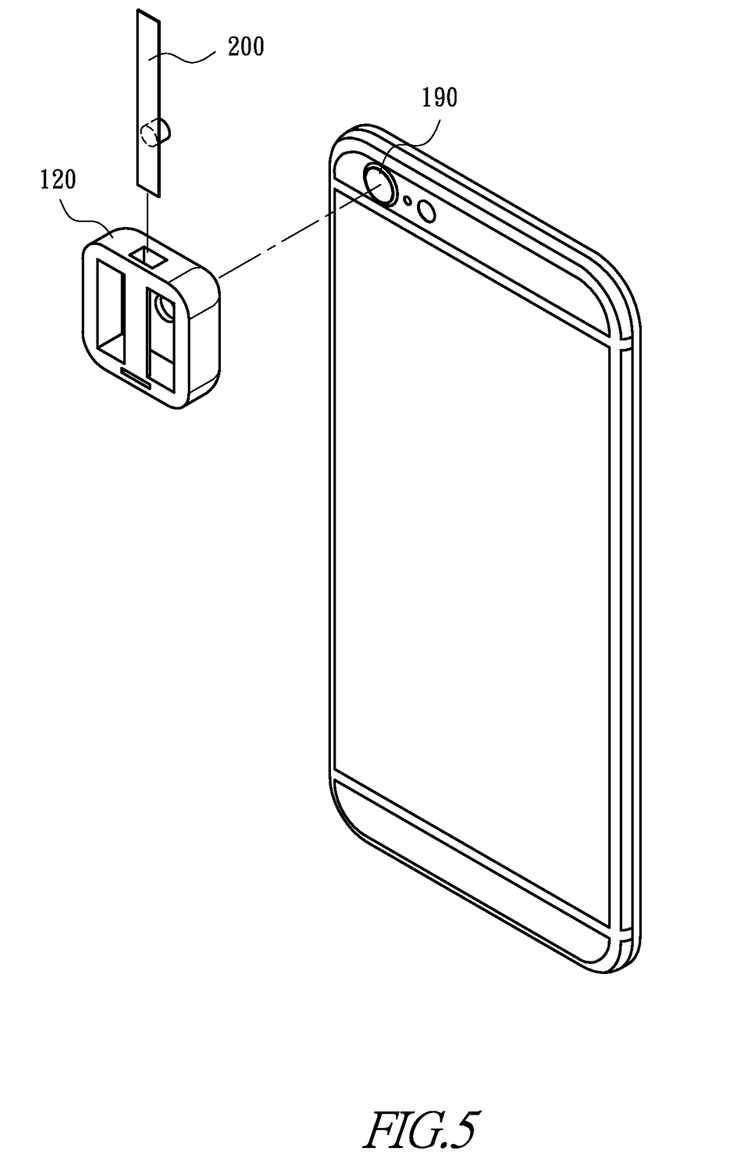
FIG. 5 illustrates a view of how the portable luminescence detector can be combined with the mobile device in the present invention.
Figure 6:
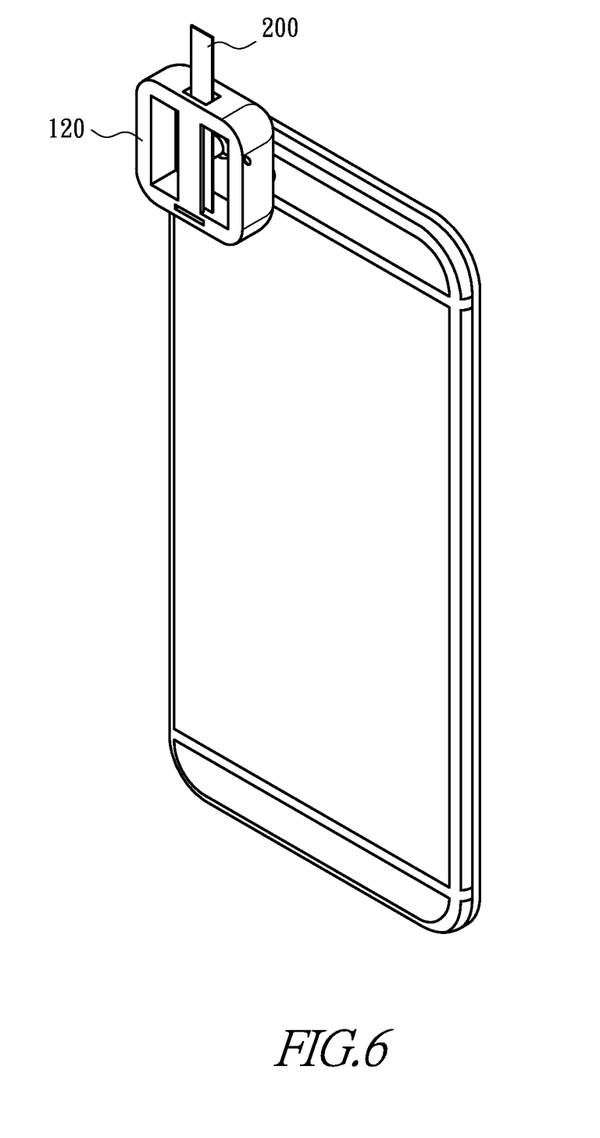
FIG. 6 illustrates a view of how the portable luminescence detector can be combined with the mobile device in the present invention.

Please refer to FIG. 5 and FIG. 6, as shown in figures, the present invention further comprises an image capturing module 190 disposed at the first side of the first main body 110, and a lens of the image capturing module 190 forms a tilted angle with the light source module 160, wherein the image capturing module 190 can be a camera of a mobile device, a digital camera, or a microscope. The image capturing module 190 works with the focusing lens module 130 to capture an image of the sample tray 200 on the second side of the first main body 110 through the through hole 111. The sample tray 200 passes through the sample tray slideway opening 151 of the first main body 110 to be disposed in the first accommodating space 140 and located between the through hole 111 and the sample tray slideway 150.

Figure 7:
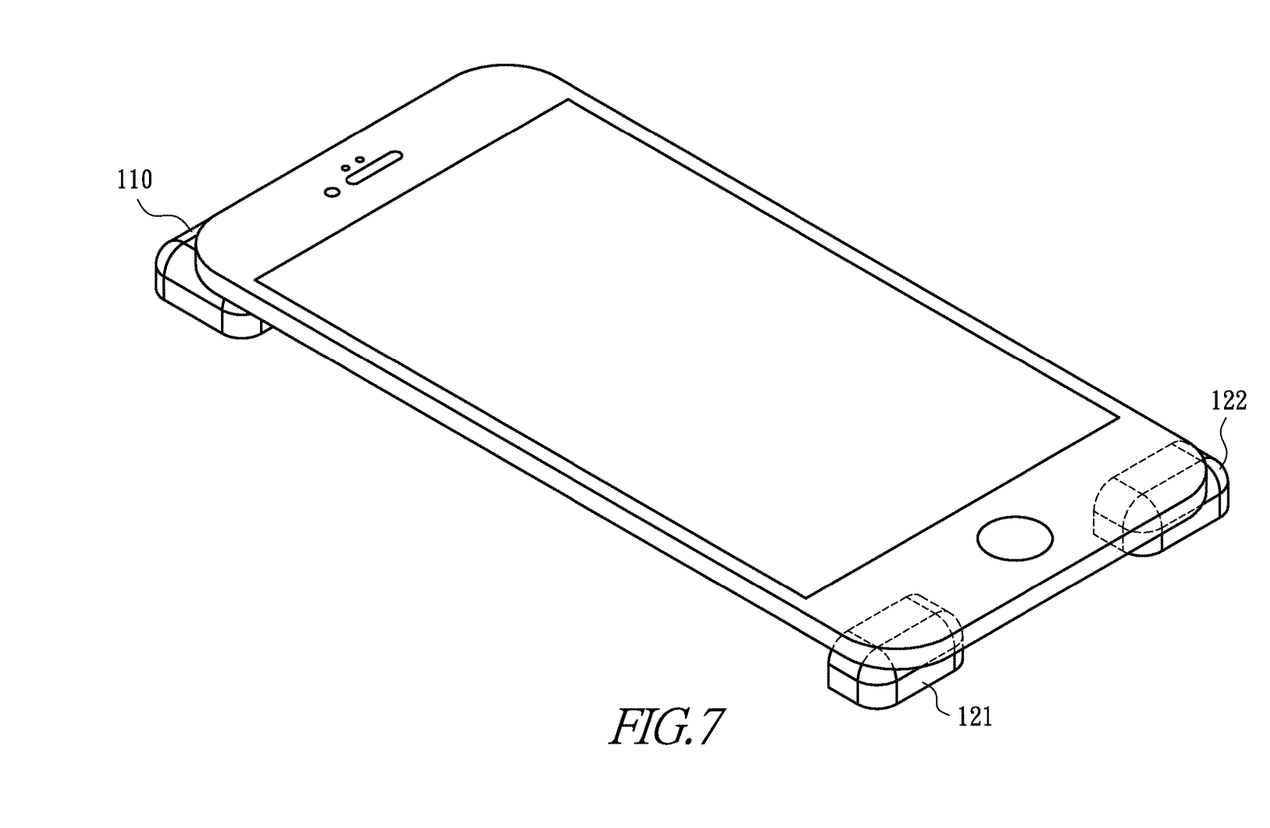
FIG. 7 illustrates a view of how the portable luminescence detector can be combined with the mobile device in the present invention.

Please refer to FIG. 7, as shown in the figure, when the portable luminescence detector of the present invention works in conjunction with the mobile device, the sample tray 200 is placed at a positions corresponding to the positions of the focusing lens 130, the through hole 111, and the image capturing module 190 position, the light source module 160 is used for providing a light source band, and then an image of the sample is captured under the light source band by the image capturing module 190 for RGB spectral analysis or real-time image RGB spectral analysis. In the present invention, the first supporting block 121 and the second supporting block 122 are placed at the fulcrums of the mobile device to keep image capturing module 190 in balance, thereby facilitating stable image capture of the image capturing module 190.

Besides, when the first main body 110 and the second main body 120 are combined into a cube, the sample tray 200 can be accommodated in the second accommodating space 170, making it more convenient for users to store and carry.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A portable luminescence detector comprising: a mobile device configured to measure a luminescence; and
    a body comprising a first main body and a second main body, wherein the first main body further comprises:
    a through hole penetrating from a first side of the first main body to a second side of the first main body;
    a focusing lens module disposed in the through hole;
    a sample tray slideway being disposed at the second side of the first main body and comprising a sample tray slideway opening corresponding to an edge of the first main body;
    a first accommodating space disposed between the second side of the first main body and the sample tray slideway; and
    a light source module disposed in the first accommodating space,
    wherein the second side of the first main body is connected with a second side of the second main body through a plurality of combining portions, and the first side of the first main body with the through hole is attached to the mobile device.

2. The portable luminescence detector as claimed in claim 1 further comprising a sample tray, wherein the sample tray slideway makes a sample tray pass through the sample tray slideway opening from an edge of the first main body to be disposed in the first accommodating space and located between the through hole and the sample tray slideway.

3. The portable luminescence detector as claimed in claim 1 further comprising an image capturing module disposed at the first side of the first main body, wherein the image capturing module works with the focusing lens module and the through hole makes an image capturing module disposed at the first side of the first main body to capture an image on the second side of the first main body through the through hole.

4. The portable luminescence detector as claimed in claim 3, wherein a lens of the image capturing module forms a tilted angle with the light source module.

5. The portable luminescence detector as claimed in claim 3, wherein the image capturing module is disposed at a mobile device, a digital camera, or a microscope.

6. The portable luminescence detector as claimed in claim 1, wherein a first side of the second main body is a plane, and a second side of second main body comprises a second accommodating space.

7. The portable luminescence detector as claimed in claim 1, wherein the plurality of combining portions can be magnets or buckles.

8. The portable luminescence detector as claimed in claim 1, wherein the second main body further comprises a first supporting block and a second supporting block, wherein the first supporting block is connected with the second supporting block through a plurality of support joints.

9. The portable luminescence detector as claimed in claim 8, wherein the plurality of support joints can be magnets or buckles.

\* \* \* \* \*